(12) United States Patent
Renner et al.

(10) Patent No.: US 6,551,239 B2
(45) Date of Patent: Apr. 22, 2003

(54) SHAFT FOR A FLEXIBLE ENDOSCOPE AND FLEXIBLE ENDOSCOPE

(75) Inventors: Martin Renner, Liptingen (DE); Uwe Bacher, Tuttlingen (DE)

(73) Assignee: Karl Storz GmbH & Co. KG (DE)

(*) Notice: Subject to any disclaimer, the term of this patent is extended or adjusted under 35 U.S.C. 154(b) by 2 days.

(21) Appl. No.: 09/771,289

(22) Filed: Jan. 26, 2001

(65) Prior Publication Data
US 2001/0056224 A1 Dec. 27, 2001

Related U.S. Application Data

(63) Continuation of application No. PCT/EP00/04761, filed on May 25, 2000.

(30) Foreign Application Priority Data

May 28, 1999 (DE) .......................... 199 24 440

(51) Int. Cl.[7] .................................. A61B 1/00
(52) U.S. Cl. ........................................ 600/139
(58) Field of Search ................ 600/139, 140, 600/121

(56) References Cited

U.S. PATENT DOCUMENTS

| | | | | |
|---|---|---|---|---|
| 4,951,497 A | * | 8/1990 | Gilibert ........................ 73/105 |
| 5,406,939 A | * | 4/1995 | Bala .......................... 206/316.1 |
| 5,423,312 A | * | 6/1995 | Siegmund et al. ........... 385/133 |
| 5,429,118 A | * | 7/1995 | Cole et al. ................... 600/121 |
| 5,643,726 A | * | 7/1997 | Tanzi et al. .................. 435/463 |
| 6,099,464 A | | 8/2000 | Shimizu et al. ............. 600/104 |
| 6,293,907 B1 | * | 9/2001 | Axon et al. .................. 600/114 |
| 2001/0029317 A1 | * | 10/2001 | Hayakawa ................... 600/140 |

FOREIGN PATENT DOCUMENTS

| | | |
|---|---|---|
| DE | 3045237 A1 | 9/1993 |
| GB | 1301393 | 12/1972 |
| JP | 8-280694 | 10/1996 |
| WO | WO99/29362 | 6/1999 |

OTHER PUBLICATIONS

"Endoskopie In Der Tiermedizin", Pferde 1995; Endoscopes in Veterinary Medicine—Horses, 1995.

* cited by examiner

Primary Examiner—Linda C. M. Dvorak
Assistant Examiner—Jocelyn Ram
(74) Attorney, Agent, or Firm—St. Onge Steward Johnston & Reens LLC

(57) ABSTRACT

A shaft is provided for a flexible endoscope. The shaft has a tubular mantle whose outer surface contacts a body tissue of a patient during use of said endoscope. The outer surface of said shaft is microscopically roughened, for example by sand blasting.

33 Claims, 2 Drawing Sheets

SHAFT FOR A FLEXIBLE ENDOSCOPE AND FLEXIBLE ENDOSCOPE

CROSSREFERENCE OF PENDING APPLICATION

This is a continuation of pending international application PCT/EP00/04761 filed on May 25, 2000 which designates the U.S.

BACKGROUND OF THE INVENTION

The present invention relates to a shaft for a flexible endoscope comprising a tubular mantle whose outer surface comes into contact with body tissue of a patient during use of the endoscope. Furthermore, the invention relates to a flexible endoscope having such a shaft.

Such flexible endoscopes with a corresponding shaft are known for example having the designation Fiberskop in the catalogue "Endoskopie in der Tiermedizin", 5th edition, 1/95 from Karl Storz GmbH & Co., Tuttlingen, Germany. In addition, fiberscopes, i.e. flexible endoscopes, are also used for various purposes in human medicine, e.g. for diagnosing respiratory passages.

Flexible endoscopes distinguish from rigid endoscopes in that the shaft of a flexible endoscope- has a flexibility such that it can take on a bent, strongly curved or even a loop-shaped form. To achieve the necessary flexibility, the shaft of a flexible endoscope normally consists of a tubular, flexible mantle, which houses the components necessary for the endoscope, such as an image transmission guide, an optical guide, an instrument channel and actuator cables. The tubular mantle normally consists of a synthetic material which is sealed at its outer side for example with one or more layers of polyurethane.

The length of the endoscope shaft, especially in veterinary medicine, can be up to 150 cm or more. In the field of human medicine, the length of the flexible endoscope shaft is normally between 15 cm and 50 cm. The outer surface of the shaft should have good glide properties as far as possible because the flexible shaft must be inserted over most of its length into an often narrow body cavity when treating a patient or an animal. This is achieved in conventional flexible endoscopes in that the endoscopes are provided with a cover lacquer which is as smooth as possible and also consists of polyurethane.

In practice, however, the glide properties of known flexible endoscope shafts have proven to be insufficient in some cases, especially with increasing lengths. In these cases, an additional glide material, for example in the form of a gel, must be used in order to insert the shaft into the body cavity as easily as possible and with as little pain as possible for the patient or animal. The glide properties of the endoscope shaft are basically improved by the use of a glide material. However, a need still exists for optimizing the glide properties of the flexible endoscope shafts as far as possible to be able to treat a patient or an animal as simply or as easily as possible. In the optimal situation, the use of an additional glide material is then no longer needed.

The object of the present invention is therefore to provide a shaft of the mentioned type whose glide properties are improved compared to previously known endoscope shafts. In addition, an object of the present invention is: to provide a corresponding flexible endosocope.

SUMMARY OF THE INVENTION

The object is achieved in that the outer surface of the shaft is microscopically roughened. The flexible endoscope according to the present invention possesses a corresponding shaft.

Roughened microscopically will be understood in that the outer surface of the shaft is roughened. to an extent which is not recognizable by the naked eye or by simple touching. Even so, the outer surface of the shaft according to the invention is uniformly rough compared to the known conventional endoscope shafts. The roughening can preferably be achieved by sand blasting, which will be discussed :in more detail below. Basically however, it is also possible to produce microscopically rough surfaces in other ways.

It has been found completely surprisingly that a microscopically roughened surface when in contact with body tissue has distinctly better glide properties than a completely smooth surface, as has been achieved conventionally using smooth lacquer layers. The rough configuration of the outer surface represents a sharp contrast to all previous measures for improving glide properties, which have always had the intention of making the outer surface as smooth as possible. A possible explanation for the surprising phenomenon is that an outer surface results from roughening which has numerous crater-like depressions. Thus the total contact surface of the outer surface with the surrounding body tissue is smaller than that when the outer surface is smooth. Independent of this attempted explanation, the mentioned feature offers a very simple and exceptionally effective possibility to improve the glide properties of flexible endoscope shafts. There is no need to use a glide material when inserting the shaft into a body. Glide materials bear the risk of allergic reactions in the body, which risk is now excluded.

In an embodiment, the outer surface is roughened by sand blasting. The feature has the advantage that the roughening takes place with a simple measure, which is controllable with conventional technologies. This feature can represent the last finishing step in the manufacture of the shaft without substantial effect on the previously performed manufacturing steps. The mentioned feature thus has the advantage that the improvement of the glide properties is particularly simple and inexpensive from the manufacturing viewpoint. A further advantage is that existing conventional endoscope shafts can be subsequently treated, so that a subsequent improvement of the glide properties of existing or even of already used endoscope shafts is possible.

In a further embodiment of the above-mentioned feature, the outer surface is roughened by sand blasting with grains having edges. Basically it is also known to roughen surfaces by sand blasting with bead-like grains, i.e. not having edges. Investigations have however shown that the improvement of the glide properties is predominant and particularly rapid when using grains having edges.

In a further embodiment of the present invention, the outer surface is roughened to have a roughness which is achievable by sand blasting with corundum 0.05 to 0.5 mm. The numbers 0.05 to 0.5 mm represent the grain size in the known manner for the corundum grains used in sand blasting. The use of other grain sizes or also grinding materials other than corundum is however generally not excluded in this embodiment of the invention.

Decisive is that a roughness of the outer surface is achieved which corresponds to that which is achievable with the aid of the mentioned feature. Namely, it has been shown that such a roughness represents a considerable improvement of the glide properties compared to previously known endoscope shafts. On the other hand, the outer surface of the endoscope shafts experience no measurable degradation with respect to sterilizability and thus the repeated use in the treatment of patients or animals. The mentioned feature is a result of empirical tests and represents an excellent improvement of the glide properties compared to previously employed flexible endoscope shafts. Very good results could also be achieved by sand blasting with glass beads 40 to 70 µm or 70 to 110 µm.

In a further embodiment, the outer surface is roughened by etching. The feature has the advantage that the roughening can take place very uniformly in simple manner. In the simplest case, the previously smooth endoscope shaft is simply placed in a suitable etching bath for a certain time. The outer surface is chemically roughened. The necessary etching agent depends on the material used in forming the outer surface. Suitable etching agents are known per se in the prior art.

In a further embodiment, the outer surface is roughened by abrasion. In contrast to sand blasting, abrasion will be understood as a mechanical roughening of the outer surface, which can be performed with a grinding disc, with sand paper or with similar abrasive means connected to a body. The feature has the advantage that the roughening can be locally specific and differentiated, where different locations on the endoscope shaft can be provided with differing degrees of roughness. For example, differing grain coarseness can be used for different regions of the shaft to generate different roughness at different locations and therefore varying glide properties.

In a further embodiment of the present invention, the outer surface consists of a material which is initially glossy and which is then roughened to an extent that it appears dull. This feature is also the result of empirical tests. Tubular mantles for endoscope shafts were employed as known from the above-mentioned catalogue from Karl Storz GmbH & Co., Tuttlingen, Germany. With these known endoscope shafts, the outer surface is formed by a transparent cover lacquer of polyurethane which appears glossy after being hardened. To improve the glide properties, these outer surfaces are preferably roughened to the extent that they appear dull.

The feature has the advantage that it represents a simple and easily controllable criterion for manufacturing endoscope shafts according to the present invention. The production of the present endoscope shafts is therefore possible without greatly interfering with the previously performed manufacturing steps. On the whole, considerable improvements in the glide properties can be achieved with the mentioned feature in simple manner.

In a further embodiment of the present invention, the tubular mantle comprises at least one base layer and a cover layer arranged thereon, where only the cover layer is roughened. The feature has the advantage that any harm to the inner mantle region of the endoscope shaft is avoided. It is also ensured that a frequent sterilization of the components of the endoscope lying within the endoscope shaft is not impaired.

According to a further embodiment of the present invention, the average roughness value $R_a$ of the roughened surface lies in the range of 0.1 to 1.6 µm. The feature has the advantage that surfaces with this average roughness value show particularly good glide properties along the tissue.

It will be understood that the above-mentioned features and those to be discussed below are applicable not only in the given combinations but also in other combinations or taken alone without departing from the scope of the present invention.

BRIEF DESCRIPTION OF THE DRAWINGS

Embodiments of the invention are illustrated in the drawings and will be discussed in more detail below.

DETAILED DESCRIPTION OF PREFERRED EMBODIMENTS

Figure 1:
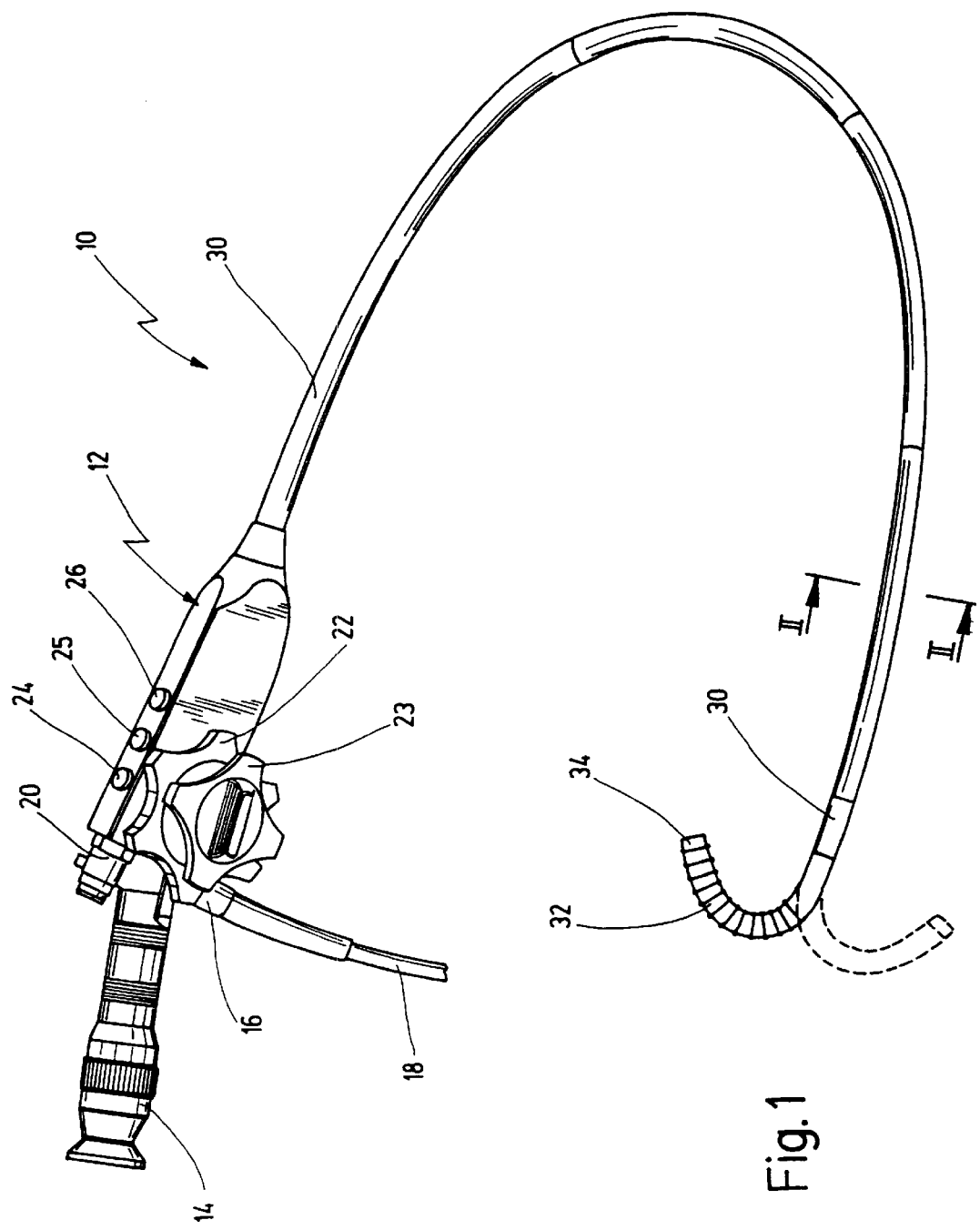
FIG. 1 shows a perspective view of a flexible endoscope according to the present invention.

A flexible endoscope according to the present invention is shown in FIG. 1 and indicated with the numeral 10. The flexible endoscope 10 comprises a head portion indicated with the numeral 12. An ocular 14 extends from the proximal end of the head portion 12. A connector 16 extending to the side serves to connect a train 18 of lines, which contain lines for illumination, flushing, insufflation, suctioning or the like. A further connector 20 extending approximately in the direction of the ocular 14 is provided, through which instruments can be inserted into the endoscope or the head portion 12, for example pincers, slings or the like.

Two hand wheels 22, 23 are arranged at the side of the head portion 12, with which the view direction of the endoscope can be adjusted as described below. In addition, switches 24, 25, 26 are arranged in the region of the head portion 12, through which various functions can be controlled, for example, suctioning, flushing or the like, which is known per se in the construction of flexible endoscopes.

An elongated flexible shaft 30 extends from the head portion 12, which in the present embodiment has a length of about 1 m. The shaft 30 is made of a flexible synthetic material, which enables a deflecting and bending of the shaft 30 as shown in FIG. 1. An end section 32 has an increased bendability compared to the shaft 30, where the end section 32 can be additionally bent by more than 180° in semicircular manner as can be taken from FIG. 1. The end section 32 can be rotated out of the position indicated by the solid lines in FIG. 1 by more than 180° while the shaft 30 remains unchanged in its orientation. This is performed by a cable mechanism which extends from an end piece 34 to the hand wheels 22, 23. A rotated position of the end section 32 is illustrated in FIG. 1 by the broken lines. This movability of the end section 32 achieved in this manner is known per se for flexible endoscopes and allows an adjustment of the view direction of the endoscope.

Figure 2:
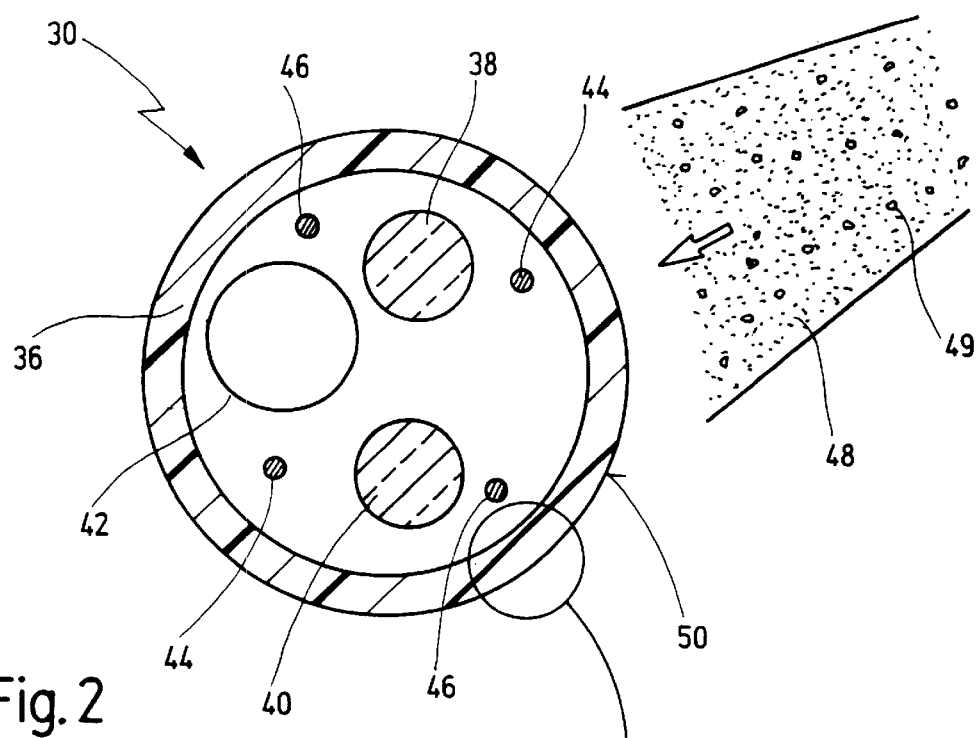
FIG. 2 shows a cross-section through the shaft of the endoscope according to the present invention taken along the line II—II in FIG. 1.

In the cross-section view of FIG. 2, the interior configuration of the shaft 30 of the endoscope 10 is shown, which is also known per se. The shaft 30 comprises a tubular mantle 36 with an image transmission guide 38, an optical guide 40, an instrument channel 42 and cables 44, 46 located in its interior. The cables 44, 46 are connected to the hand wheels 22, 23 and enable the described movement of the end section 32.

A sand blasting of the outer surface 50 is indicated schematiscally with the numeral 48. The outer surface 50 is microscopically roughened by the sand blasting 48. The glide properties of the outer surface 50 of the mantle 36 and therefore the glide properties of the shaft 30 are improved in this manner. Preferably, sand blasting 48 for this purpose takes place with grains 49 having edges.

In a particularly preferred embodiment, the outer surface 50 of the mantle 36 is roughened by sand blasting 48 with corundum 0.12 to 0.25 mm. The numbers 0.12 to 0.25 mm as mentioned above relate to the grain size of the employed grains 49. Such grain sizes are well known in the field of sand blasting. In an alternative embodiment, the outer surface 50 of the mantle 36 is roughened by sand blasting with glass beads 40 to 70 μm or 70 to 110 μm.

Contrary to the schematic illustration in FIG. 2, the sand blasting 48 of the outer surface 50 preferably takes place at a time when the image transmission guide 38, the optical guide 40, the instrument channel 42 and the cables 44, 46 are not yet assembled in the shaft 30.

In an alternative embodiment of the present invention, the outer surface 50 is roughened by etching in a suitable etching bath or by abrasion with a suitable grinding body, for example a grinding disc.

The roughness characteristics (according to the German industry standard DIN 4768 T1; 8.74) of roughened shafts of fiberscopes of the applicant are listed in the following Table 1, which were roughened with different roughening means.

Shaft 1: glass beads 40 to 70 μm
Shaft 2: glass beads 70 to 110 μm
Shaft 3: corundum 0.12–0.25 mm

TABLE 1

Roughness characteristics (DIN 4768 T1; 8.74)

|  | Shaft 1 | Shaft 2 | Shaft 3 |
| --- | --- | --- | --- |
| $R_a$ | 0.42 μm | 0.70 μm | 0.9 μm |
| $R_z$ | 2.5 μm | 4.20 μm | 5.30 μm |
| $R_{max}$ | 3.3 μm | 5.2 μm | 6.5 μm |

Figure 3:
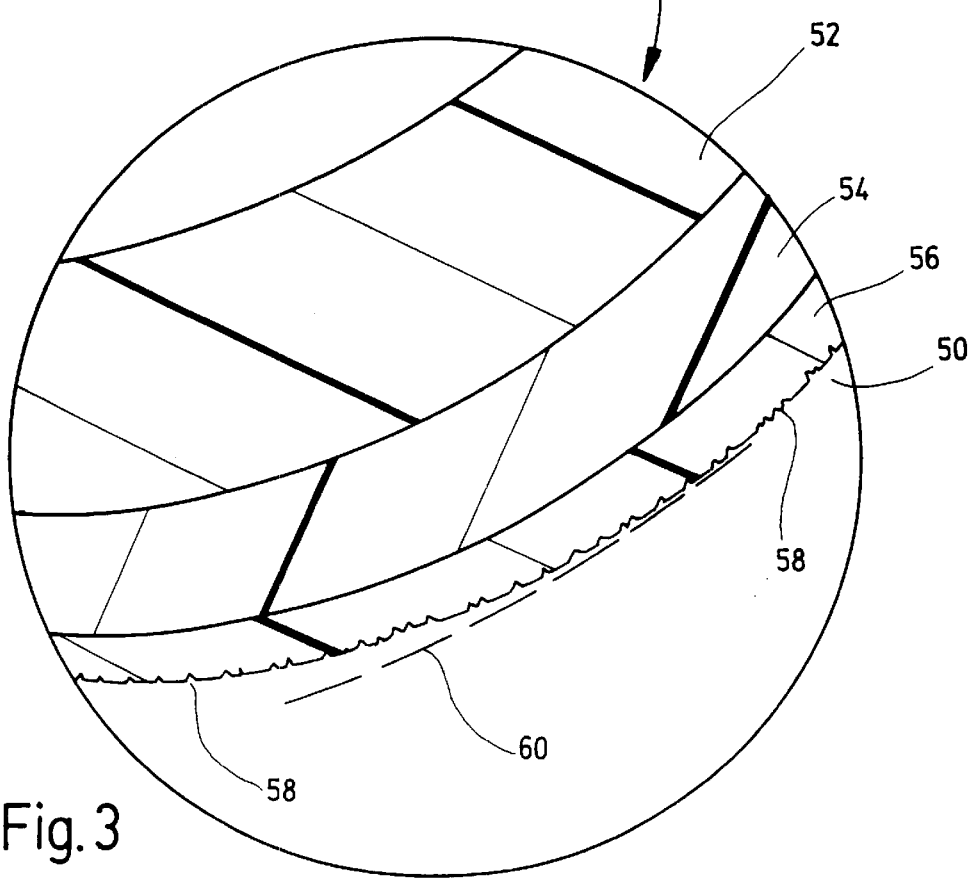
FIG. 3 shows a greatly enlarged illustration of the tubular mantle of the flexible endoscope of FIG. 2.

$R_a$ = average roughness value
$R_z$ = roughness depth
$R_{max}$ = maximum roughness depth As can be taken from the enlarged representation of FIG. 3, the outer surface 50 of the mantle 36 is roughened by sand blasting 48. In addition, this enlarged view shows that the mantle 36 comprises a first base layer 52 consisting of a flexible synthetic material. This first base layer 52 forms the load-carrying inner region of the mantle 36. A second base layer 54 seals the first base layer 52 on the outside. The second base layer 52 in the present embodiment consists of a soft polyurethane.

A preferred embodiment, not shown here for reasons of clarity, includes a second base layer 54 of three individual polyurethane layers, which decrease in hardness from the inside of the mantle 36 to the outside. A cover layer 56 is applied to the outside of the outermost base layer 54. The cover layer 56 consists of a transparent cover lacquer, which after hardening initially forms a very smooth, glossy surface 50. This surface 50 is subsequently roughened microscopically by the sand blasting 48 or by the alternative possibilities indicated in FIGS. 2 and 3.

In a preferred embodiment of the present invention, the outer surface 50 of the mantle 36 is roughened to the extent that the outer surface 50 appears to be dull. On the microscopic level, this leads to the fact that the outer surface 50 contains crater-like depressions 58.

The surface of a body tissue is indicated schematically with the numeral 60, which comes into contact with the outer surface 50 when using the present endoscope 10. As illustrated, the roughening of the outer surface 50 has the consequence that the body tissue 60 no longer comes into contact with the crater-like depressions 58, but only with the plateaux lying therebetween. In this manner, the total contact surface is reduced when compared to the conditions with the previously known endoscope shafts 30. Consequently, the shaft 30 of the endoscope 10 of the present invention possesses improved glide properties.

The pressure and the duration for applying sand blasting 48 to the outer surface 50 of the mantle 36 is preferably determined empirically, namely such that the previously glossy surface 50 of the cover layer 56 appears to be uniformly dull after sand blasting 48.

What is claimed is:

1. A shaft adapted for a flexible endoscope, comprising:

a tube having an outer surface adapted to be in contact with a body tissue of a patient; and said outer surface includes a plurality of depressions of microscopic width, depth, and length;

wherein said plurality of depressions reduces friction as said tube slides along the body tissue.

2. The shaft of claim 1, wherein said outer surface is roughened by sand blasting.

3. The shaft of claim 1, wherein said outer surface is roughened by a plurality of grains having a plurality of edges.

4. The shaft of claim 1, wherein said outer surface is roughened to a roughness which is achievable by sand blasting with a corundum 0.05 to 0.5 mm.

5. The shaft of claim 1, wherein said outer surface is roughened by etching.

6. The shaft of claim 1, wherein said outer surface is roughened by abrasion.

7. The shaft of claim 1, wherein said outer surface is made of a material being initially glossy, and wherein said outer surface is roughened to the extent that it appears dull.

8. The shaft of claim 1, wherein said tubular mantle comprises at least one inner base layer and an outer cover layer, wherein only said outer cover layer is roughened.

9. The shaft of claim 1, wherein an average roughness value $R_a$ of said outer surface lies in a range of 0.1 μm to 1.6 μm.

10. A flexible endoscope having a shaft, comprising:

a tube having an outer surface adapted to be in contact with a body tissue of a patient; and said outer surface includes a plurality of depressions of microscopic width, depth, and length;

wherein said plurality of depressions reduces friction as said tube slides along the body tissue.

11. The flexible endoscope of claim 10, wherein said outer surface of said shaft is roughened by sand blasting.

12. The flexible endoscope of claim 10, wherein said outer surface is roughened by a plurality of grains having a plurality of edges.

13. The flexible endoscope of claim 10, wherein said outer surface of said shaft is roughened to a roughness which is achievable by sand blasting with a corundum 0.05 to 0.5 mm.

14. The flexible endoscope of claim 10, wherein said outer surface of said shaft is roughened by etching.

15. The flexible endoscope of claim 10, wherein said outer surface of said shaft is roughened by abrasion.

16. The flexible endoscope of claim 10, wherein said outer surface of said shaft is made of a material that is initially glossy, and wherein said outer surface of said shaft is roughened to the extent that it appears dull.

17. The flexible endoscope of claim 10, wherein said tube of said shaft comprises at least one inner base layer and an outer cover layer, wherein only said outer cover layer is roughened.

18. The flexible endoscope of claim 10, wherein an average roughness value $R_a$ of said outer surface of said shaft lies in a range of 0.1 μm to 1.6 μm.

19. A shaft adapted for a flexible endoscope, comprising:
a tube having an outer surface adapted to be in contact with a body tissue of a patient;
said outer surface includes a plurality of depressions; and
said plurality of depressions have an average roughness value of approximately 0.1 μm to approximately 1.6 μm;
wherein said plurality of depressions reduces friction as said tube slides along the body tissue.

20. A method for providing a shaft adapted for a flexible endoscope, comprising the steps of:
providing a tube having an outer surface adapted to be in contact with a body tissue of patent; and
providing a plurality of depressions of microscopic width, depth, and length on the outer surface;
wherein said plurality of depressions reduces friction as said tube slides along the body tissue.

21. The method according to claim 20, further comprising the step of sand blasting the outer surface to provide the plurality of depressions of microscopic width, depth, and length.

22. The method according to claim 21, further comprising the step of using a plurality of grains having a plurality of edges to sand blast the outer surface.

23. The method according to claim 21, further comprising the step of using a corundum of between approximately 0.05–0.5 mm to sand blast the outer surface.

24. The method according to claim 20, further comprising the step of etching the outer surface.

25. The method according to claim 20, further comprising the step of dulling the outer surface.

26. The method according to claim 20, further comprising the step of providing an inner base layer and an outer cover layer on the tube and providing the plurality of depressions on the outer cover layer.

27. A method for providing a flexible endoscope having a shaft, comprising the steps of:
providing a tube having an outer surface adapted to be in contact with a body tissue of a patient; and
providing a plurality of depressions of microscopic width, depth, and length on the outer surface;
wherein said plurality of depressions reduces friction as said tube slides along the body tissue.

28. The method according to claim 27, further comprising the step of sand blasting the outer surface to provide the plurality of depressions of microscopic width, depth, and length.

29. The method according to claim 28, further comprising the step of using a plurality of grains having a plurality of edges to sand blast the outer surface.

30. The method according to claim 28, further comprising the step of using a corundum of between approximately 0.05–0.5 mm to sand blast the outer surface.

31. The method according to claim 27, further comprising the step of etching the outer surface.

32. The method according to claim 27, further comprising the step of dulling the outer surface.

33. The method according to claim 27, further comprising the step of providing an inner base layer and an outer cover layer on the tube and providing the plurality of depressions on the outer cover layer.

* * * * *